(12) United States Patent
Bailey et al.

(10) Patent No.: US 9,268,405 B2
(45) Date of Patent: Feb. 23, 2016

(54) ADAPTIVE GESTURE-BASED METHOD, SYSTEM AND COMPUTER PROGRAM PRODUCT FOR PREVENTING AND REHABILITATING AN INJURY

(75) Inventors: Gemma M. Bailey, Eastleigh (GB); Leon Chen, Bournemouth (GB); James K. Hook, Knowle (GB); Melanie S. Hopper, Winchester (GB); Susannah Marie Lindsay, Towcester (GB)

(73) Assignee: International Business Machines Corporation, Armonk, NY (US)

( * ) Notice: Subject to any disclaimer, the term of this patent is extended or adjusted under 35 U.S.C. 154(b) by 698 days.

(21) Appl. No.: 13/523,934

(22) Filed: Jun. 15, 2012

(65) Prior Publication Data

US 2013/0339908 A1 Dec. 19, 2013

(51) Int. Cl.
| | |
|---|---|
| G06F 3/01 | (2006.01) |
| G06F 3/048 | (2013.01) |
| G01H 11/00 | (2006.01) |
| H04B 5/00 | (2006.01) |
| G06F 17/30 | (2006.01) |
| G06F 3/0484 | (2013.01) |
| A61B 5/11 | (2006.01) |

(52) U.S. Cl.
CPC .............. G06F 3/017 (2013.01); G06F 3/0484 (2013.01); *A61B 5/11* (2013.01); *A61B 5/1116* (2013.01); *A61B 5/1121* (2013.01); *A61B 5/1124* (2013.01)

(58) Field of Classification Search
CPC ... G06F 3/04883; G06F 3/017; G06F 3/0481; G06F 3/0488; G06F 2203/04807; G06F 3/048; G06F 3/01; G06F 17/30; H04B 5/00; G01H 11/00
USPC .......................................................... 715/863
See application file for complete search history.

(56) References Cited

U.S. PATENT DOCUMENTS

| | | | | |
|---|---|---|---|---|
| 6,142,910 | A * | 11/2000 | Heuvelman | ........................ 482/4 |
| 6,190,287 | B1 | 2/2001 | Nashner | |
| 6,650,313 | B2 | 11/2003 | Levine et al. | |
| 2003/0214481 | A1* | 11/2003 | Xiong | ........................... 345/157 |
| 2004/0119682 | A1 | 6/2004 | Levine et al. | |
| 2006/0103731 | A1* | 5/2006 | Pilu et al. | ................. 348/207.99 |

(Continued)

FOREIGN PATENT DOCUMENTS

| | | | |
|---|---|---|---|
| IS | WO2011004403 | * | 1/2011 |
| WO | 2011004403 | A1 | 1/2011 |

OTHER PUBLICATIONS

Shah, Healthy Breaks, Jan. 2011, BenedIT Magazine, pp. 14-17.*

(Continued)

*Primary Examiner* — Jennifer To
*Assistant Examiner* — Hugo Molina
(74) *Attorney, Agent, or Firm* — Maeve McCarthy; Jason Sosa (57) ABSTRACT

In an approach to allowing a user to operate a computing device while preventing and/or rehabilitating an injury, three-dimensional gestures of a user are translated into corresponding movement of a cursor on a display device. Different gestures can indicate the same motion of the cursor. As the user gestures to move the cursor, the software determines, based on a history of use specific to the user, whether the user can continue without feeling pain or fatigue. If it is determined that continued use will cause or is likely to cause pain or fatigue, the software can request the user to take a break, or can switch the gesture or motion required by the user to move the cursor in a similar manner.

20 Claims, 4 Drawing Sheets

(56) References Cited

U.S. PATENT DOCUMENTS

| | | | | |
|---|---|---|---|---|
| 2006/0166620 | A1* | 7/2006 | Sorensen | 455/41.1 |
| 2007/0299371 | A1* | 12/2007 | Einav et al. | 601/5 |
| 2008/0266250 | A1* | 10/2008 | Jacob | 345/156 |
| 2009/0295733 | A1* | 12/2009 | Stenbroten | 345/168 |
| 2010/0131605 | A1* | 5/2010 | Firminger et al. | 709/206 |
| 2010/0306710 | A1* | 12/2010 | Poot | 715/856 |
| 2010/0316299 | A1* | 12/2010 | Lee et al. | 382/209 |
| 2011/0093820 | A1* | 4/2011 | Zhang et al. | 715/863 |
| 2012/0133655 | A1* | 5/2012 | Kristjansson | 345/419 |
| 2012/0235916 | A1* | 9/2012 | Atzmon | 345/168 |
| 2012/0320080 | A1* | 12/2012 | Giese et al. | 345/619 |
| 2013/0066859 | A1* | 3/2013 | Young | 707/723 |
| 2013/0294651 | A1* | 11/2013 | Zhou et al. | 382/103 |
| 2013/0331993 | A1* | 12/2013 | Detsch et al. | 700/275 |

OTHER PUBLICATIONS

Anyware Ltd, "PastTense—Aviod Carpal Tunnel Syndrome—Trial Free Reminder Software", anyware.co, Copyright 1998, 1999 [online], [retrieved on Mar. 13, 2012]. Retrieved from the Internet <URL: http://www.anyware.co.nz/pasttense/>.

Chequers Software Ltd, "Break Reminder is Work and Home RSI Prevention and Repetitive Stress Injury Take a Break, Micropause, Stretch and Exercise Treatment Reminder Computer Software", cheqsoft.com, Copyright 2000-2007, Last Revised Dec. 15, 2007 [online], [retrieved on Mar. 13, 2012]. Retrieved from the Internet <URL: http://www.cheqsoft.com/break.html#top>.

Cyberflair Ltd, "CyberFlair Software Home Page", cyberflair.com, Copyright 2010-2012 [online], [retrieved on Mar. 13, 2012]. Retrieved from the Internet <URL: http://www.cyberflair.com/>.

Einspine Ltd, "How Desk Doctor Works to Safeguard Upper Body Health", einspine.com, Copyright 2006 [online], [retrieved on Mar. 13, 2012]. Retrieved from the Internet <URL: http://www.einspine.com/deskdoctor/1_overview.html>.

IBM, "Pattern Collections", Apr. 14, 2009, IP.com [online], [retrieved on Mar. 13, 2012]. Retrieved from: Prior Art Database, IP.com No. IPCOM000181813D.

Kumsoft.com, "Kum Soft", kumsoft.com [online], [retrieved on Mar. 13, 2012]. Retrieved from the Internet <URL:http://www.kumsoft.com/killrsi.html>.

Montrose Secam Limited, "Welcome to Montrose Secam Ltd", montrosesecam.com [online], [retrieved on Feb. 28, 2012]. Retrieved from the Internet <URL: http://www.montrosesecam.com/>.

Pimentel, "Helping Hand for Those With Shaky Hands / IBM to Unveil Mouse Adapter to Steady Cursor", sfgate.com, Mar. 14, 2005, Hearst Communications [online], [retrieved on May 17, 2012]. Retrieved from the Internet <URL:http://www.sfgate.com/cgi-bin/article.cgi?f=/c/a/2005/03/14/BUGCIBO7E01.DTL>.

Remedy Interactive Inc, "RSIGuard | Desktop Ergonomic Software", rsiguard.com, Copyright 2011 [online], [retrieved on Mar. 13, 2012]. Retrieved from the Internet <URL: http://www.rsiguard.com/>.

RSIbreak, "RSIBreak—Welcome", rsibreak.org, Copyright 2012 [online], [retrieved on Mar. 13, 2012]. Retrieved from the Internet <URL: http://www.rsibreak.org/>.

Workrave.org, "Workrave", workrave.org [online], [retrieved on Mar. 13, 2012]. Retrieved from the Internet <URL: http://www.workrave.org/>.

* cited by examiner

ADAPTIVE GESTURE-BASED METHOD, SYSTEM AND COMPUTER PROGRAM PRODUCT FOR PREVENTING AND REHABILITATING AN INJURY

FIELD OF THE INVENTION

The present invention relates generally to the field of computerized gesture recognition, and more particularly to, safely and without injury, moving a cursor on a display device based on received gestures from a user.

BACKGROUND OF THE INVENTION

The use of computing devices is integrated into the lives of many individuals. For example, it is common for students to bring laptops into class to take notes; adults often spend the majority of each work day on a computer; and at the end of the day, adults and youth alike often spend a large portion of their evening on their respective computers. Performing various functions and operations of a computing device typically requires frequent and repetitive small motions on the part of a user utilizing conventional input devices (e.g., a mouse and keyboard). Due to these motions, regular users of computing devices are at a heightened risk of repetitive strain injury (RSI) and carpal tunnel syndrome.

To combat such deleterious effects, existing programs can prompt a user to take regular breaks and suggest a user to perform various stretching exercises. Additionally, for users who have already suffered such an injury, existing programs can also assess a user's range of motion and suggest exercises to aid in recovery. It is also known for programs to facilitate use of a computer for users that have difficulty using conventional input devices, for example, those who have suffered injuries such as joint damage, muscular damage, or nerve damage.

SUMMARY

Embodiments of the present invention disclose a method, computer program product and computer system for preventing and/or rehabilitating an injury when operating a computing device. A computer tracks, via one or more sensor devices connected to the computer, one or more gestures performed by a user to control a cursor on a display device. In response, the computer moves the cursor on the display device in a manner which corresponds to the one or more gestures. Based on an analysis of the one or more gestures, the computer determines whether a subsequent performance of one or more of the one or more gestures are potentially injurious, and if so, the computer takes a preventative action such that the user has the opportunity to recover or avoid injury.

DETAILED DESCRIPTION

Figure 1:
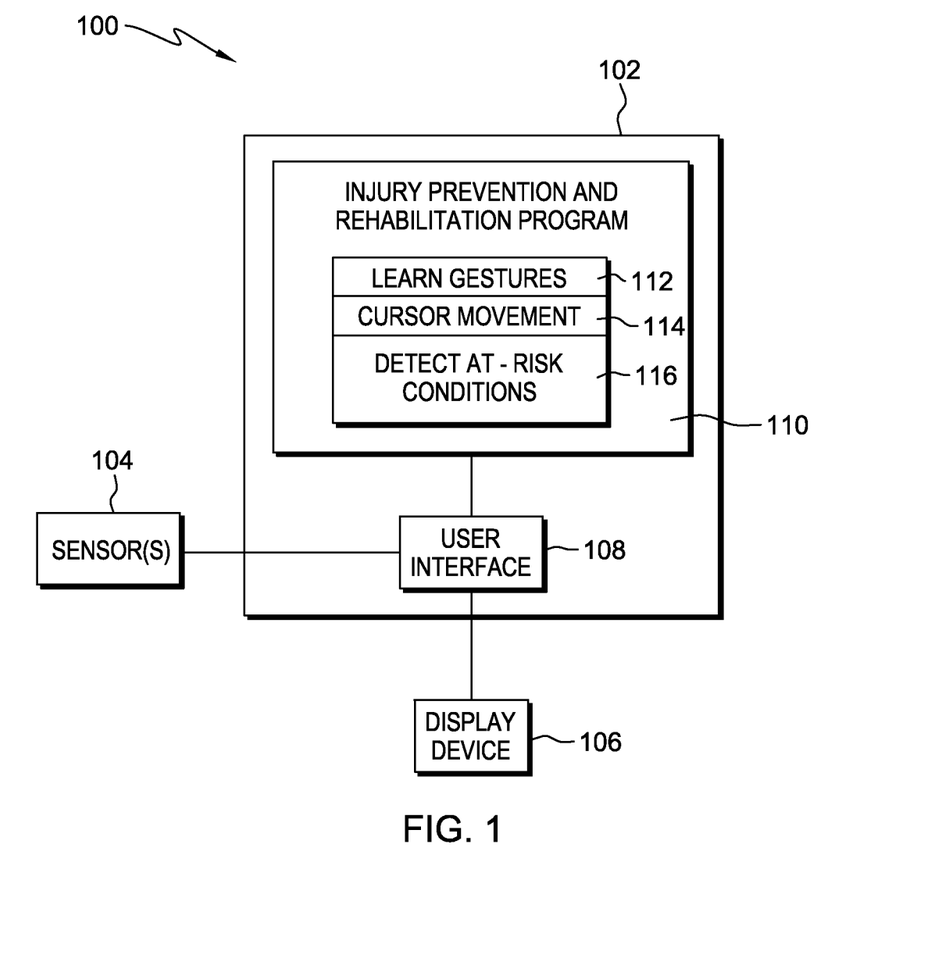
FIG. 1 is a block diagram of a data processing system according to an embodiment of the present invention.

The present invention will now be described in detail with reference to the Figures. FIG. 1 illustrates a data processing system, generally designated 100, according to one embodiment of the present invention.

In the illustrated embodiment, data processing system 100 comprises computing device 102 connected to sensor(s) 104 and display device 106. Computing device 102 may be a server computer, a client computer, a notebook computer, a laptop computer, a tablet computer, a handheld device or smart-phone, a thin client, or any other electronic device or computing system capable of receiving input from a user, performing computational operations, and displaying data. In another embodiment, computing device 102 represents a computing system utilizing clustered computers and components to act as a single pool of seamless resources when accessed through a network. This is a common implementation for datacenters and for cloud computing applications.

Computing device 102 contains user interface 108 for receiving input from sensor(s) 104 and displaying data on display device 106. User interface 108 may be, for example, a graphical user interface (GUI) or a web user interface (WUI). Sensor(s) 104 may be any device or group of devices that can be used to detect gestures performed by a user. A "gesture" is herein defined as any detectable movement of the body or part of the body. Gestures are tracked by sensor(s) 104, typically as a plurality of data points relayed to computing device 102. In one embodiment, the sensors transfer the data via a message protocol such as Message Queue Telemetry Transport (MQTT). In one embodiment, sensor(s) 104 include one or more cameras that can distinguish a user and/or appendages of the user by way of various image-based recognition techniques (e.g., light contrast, time-of-flight measuring, etc.) and track a change in position of any identified images. In another example, sensor(s) 104 may be embodied in a controller that may be held by a user, or in a preferred embodiment, physically attached to the user or appendage of the user. Such a controller would include at least one accelerometer such that a gesture may be detected by the change in acceleration over time. In the preferred embodiment, sensor(s) 104 include at least one accelerometer and at least one gyroscope such that complex motions and gestures can be detected and relevant data points representing the performed gestures can be relayed to computing device 102 via user interface 108. Other techniques for tracking motions of a user may be used. Performed gestures are translated by injury prevention and rehabilitation program 110 into corresponding cursor movement for display on display device 106.

Injury prevention and rehabilitation program 110 has the capability to prevent and/or rehabilitate an injury to a user while the user is operating computing device 102. Embodiments of the present invention recognize that moving a cursor in response to a wide range of gestures, as opposed to the limited two-dimensional movements of a mouse, allows for more complex gestures and a greater range of motion. As such, injury prevention and rehabilitation program 110 allows the user to move the cursor with gestures that are safer than the small repetitive motions required by a mouse. Additionally, injury prevention and rehabilitation program 110 may aid in rehabilitation by suggesting and allowing control of the cursor with gestures that are beneficial to a user already suffering an injury. For example, certain motions may be known to strengthen or increase flexibility of an injured muscle or joint. Injury prevention and rehabilitation program 110 may associate such a rehabilitative or preventative gesture to movement of the cursor (e.g., direction of movement, pattern of movement, length of movement, etc.). Subsequent movement of the cursor may then require that the rehabilitative or preventative gestures be performed.

Embodiments of the present invention further recognize that even gestures which are "safe" or "rehabilitative" to a user may, with repeated use, cease to produce the same benefits, or even become harmful. For example, gestures that help an injury heal, if done too often in a short amount of time, may actually worsen the injury. As another example, gestures with a large range of motion may, over time, still put a user at risk of repetitive strain injury. As such, injury prevention and rehabilitation program 110 allows different gestures to correspond to the same movement of the cursor. Thus a user can continue to safely use the computer, or more accurately to move the cursor of the computer, by switching the gesture required to affect the same movement. Each gesture or set of gestures corresponding to a given cursor movement or set of cursor movements may be referred to as a movement profile. In a preferred embodiment, injury prevention and rehabilitation program 110 includes at least two movement profiles.

Injury prevention and rehabilitation program 110 may require a certain gesture or set of gestures, i.e., a certain movement profile, to move the cursor in a way that is rehabilitative for a specific injury. In the preferred embodiment, multiple movement profiles exist for the specific injury. For example, if a user has a shoulder injury, different gestures might affect the joint and the muscles surrounding the joint in different ways. One movement profile might require gestures that stretch the proper muscles and tendons, while a second movement profile might require gestures aimed at strengthening the muscles. Additionally, different movement profiles may be created and/or assessed at different difficulty levels.

The different movement profiles may be defined either by being pre-programmed into injury prevention and rehabilitation program 110, or, in the preferred embodiment, may be defined by the user. Where the user defines his or her own gestures, the user may, in one embodiment, pick a gesture from a list of suggested gestures to correspond to a specific cursor movement. In another example, the user can "train" the cursor to correspond to a gesture in a specific way. This could be done through a learning functionality in injury prevention and rehabilitation program 110, e.g., learn gestures program 112. Such an embodiment is described with more detail in FIG. 3. Under the preferred embodiment, the user could create gesture/cursor movement associations that are comfortable specifically to the user or recommended by a physical therapist or medical professional specifically for an injury. As sensor(s) 104 detect user gestures and send corresponding data points to user interface 108, cursor movement program 114 (another functionality of injury prevention and rehabilitation program 110) translates the detected gestures to the proper corresponding cursor movement according to the applicable movement profile.

Injury prevention and rehabilitation program 110 also determines a threshold for when gestures of a certain movement profile have become potentially harmful or injurious. Injury prevention and rehabilitation program 110 uses indications of fatigue and/or pain to determine this threshold. Injury prevention and rehabilitation program 110 contains a functionality for detecting such conditions, e.g., detect at-risk conditions program 116, and various methods of this functionality are discussed subsequently with regard to FIG. 3. During operation of injury prevention and rehabilitation program 110, the injury prevention and rehabilitation program determines whether a user is approaching, or has reached, the threshold, and takes a preventative action to prevent injury to the user. The preventative action may include requesting the user to take a break or switching to a different movement profile.

Figure 4:
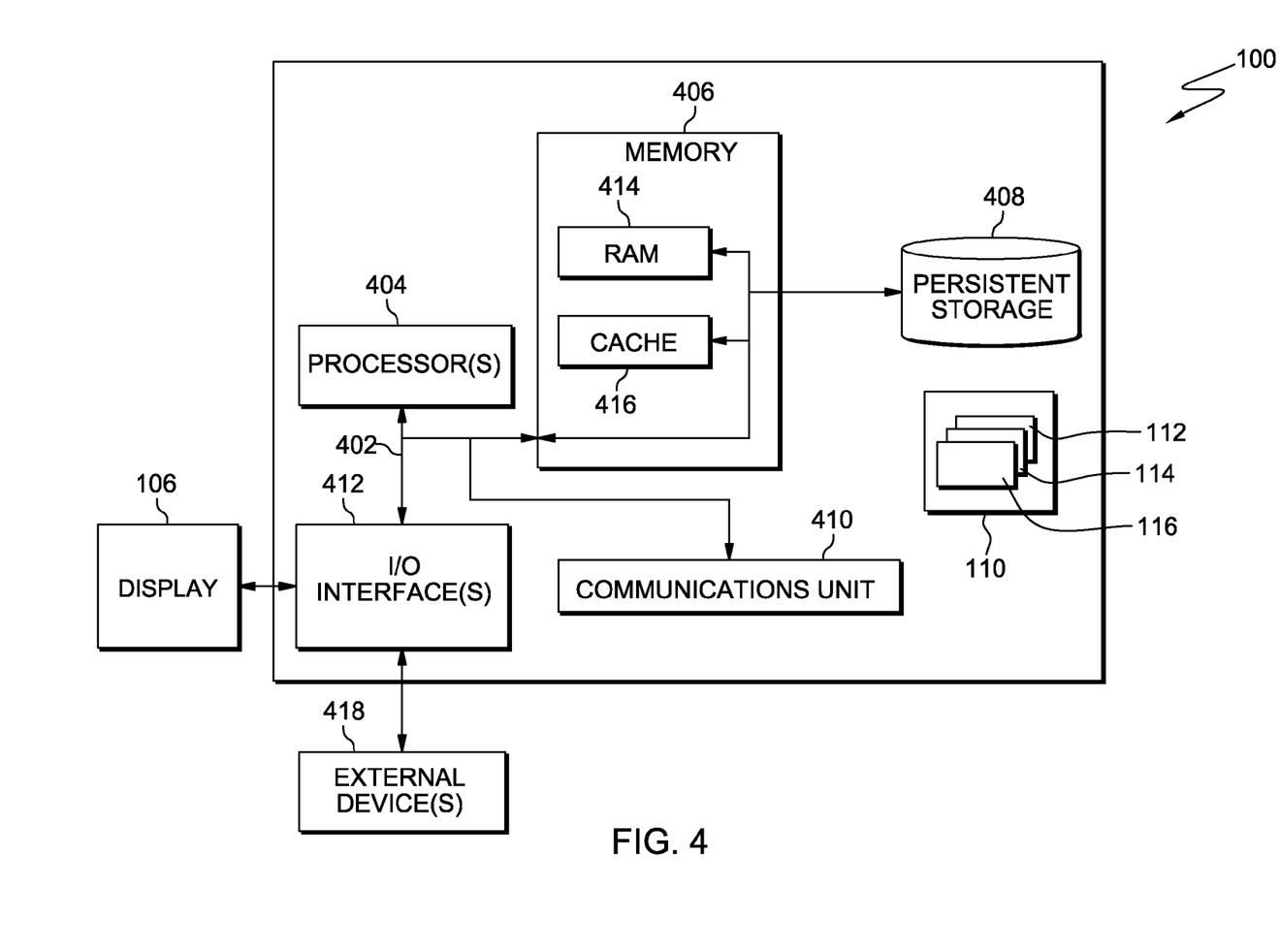
FIG. 4 depicts a block diagram of components of the data processing system of FIG. 1, in accordance with an illustrative embodiment.

Data processing system 100 contains various internal and external components depicted in FIG. 4.

Figure 2:
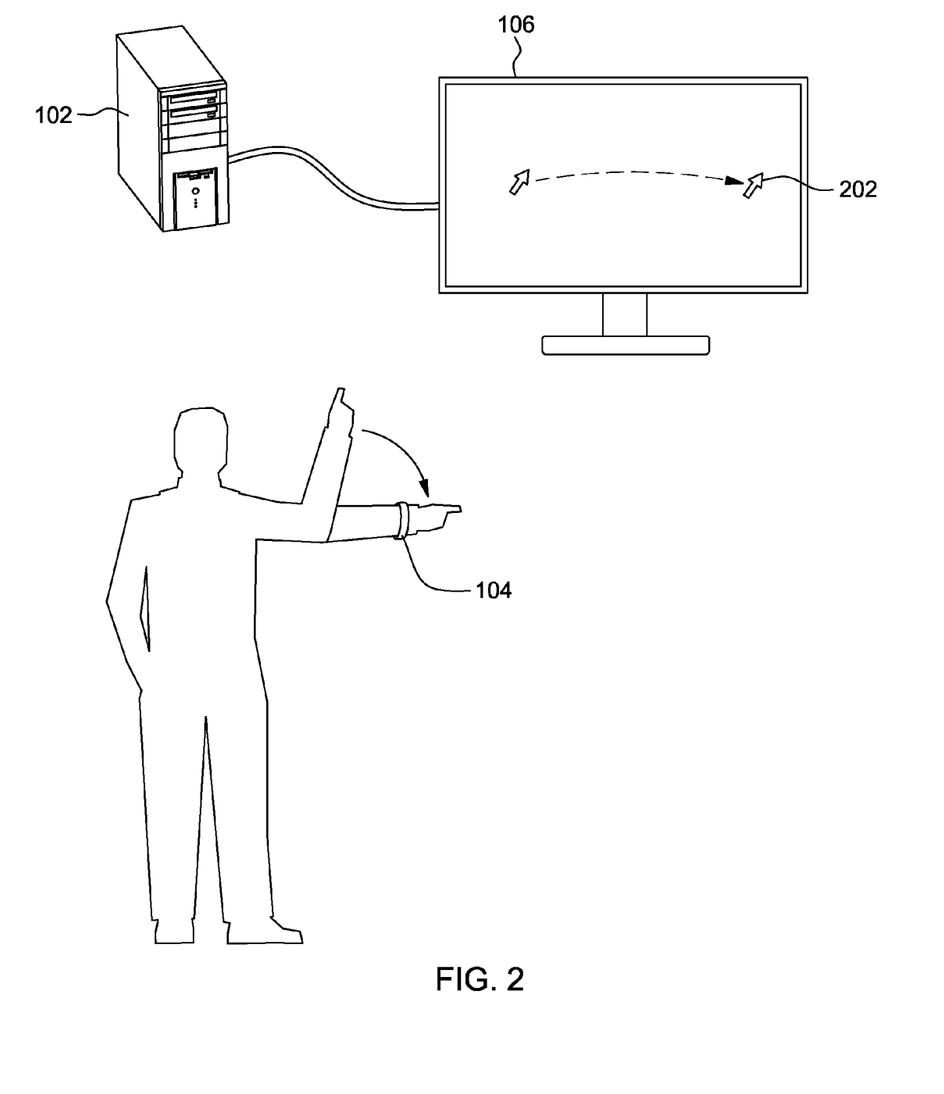
FIG. 2 illustrates an example of a cursor moving in response to a user gesture.

FIG. 2 illustrates cursor 202 moving in response to a user gesture. The user gesture is detected by sensor(s) 104. In the depicted example, sensor(s) 104 are attached to a user's arm. The detected gestures are relayed back to computing device 102, and cursor 202 moves in a corresponding manner on display device 106. Though the movement of cursor 202 corresponds to a performed gesture, the movement of the cursor need not mirror the gesture. In one embodiment, if the movement of cursor 202 does mirror a gesture performed, the ratio of gesture movement to cursor movement is greater than one-to-one. For example, if display device 106 measures twelve inches across, moving cursor 202 from one side of the display device to another may require a user to move his or her hand twenty-four inches from one side to another. In this manner, a user may manipulate the cursor with more natural and larger amplitude movements. In another embodiment, the ratio of gesture movement to cursor movement is less than one-to-one. In a situation where large movements are painful to the user, for example, small gestures affecting a greater range of cursor movement can prevent pain and/or optimize comfort.

Figure 3:
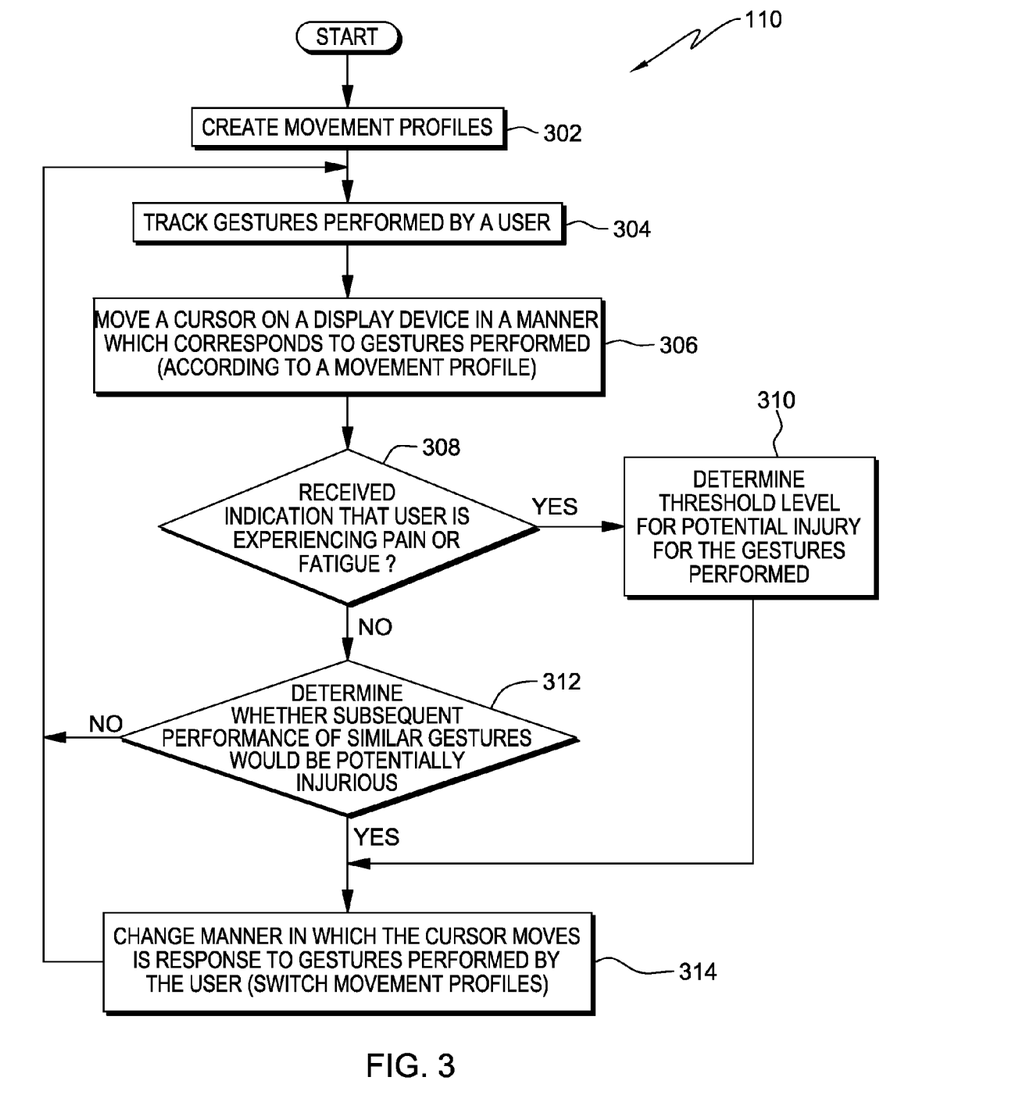
FIG. 3 depicts the operational steps of an injury prevention and rehabilitation program, in accordance with an embodiment of the present invention.

FIG. 3 depicts the operational steps of injury prevention and rehabilitation program 110 in accordance with an embodiment of the present invention.

In the preferred embodiment, injury prevention and rehabilitation program 110 creates a plurality of movement profiles (step 302), each movement profile being a manner in which a cursor moves in response to gestures performed by the user. In one embodiment, cursor movement follows/mirrors the movement of a gesture performed by a user, and each movement profile comprises a ratio of distances moved by a gesture and the corresponding distance to be moved by the cursor. For example, a user may find it convenient to make small pointing gestures to direct the cursor. The ratio allowing these small motions to be effective may be saved as one movement profile. For safety purposes, however, a second movement profile requiring large exaggerated movements may be used, allowing the user to recover and/or rest when needed.

In the preferred embodiment, complex patterns of three-dimensional gestures may be learned by injury prevention and rehabilitation program 110, for example, by performing a statistical analysis on data collected from sensor(s) 104. Recognized gestures/movements would be mapped to a cursor movement. One exemplary implementation capable of building a statistical model reflecting these patterns is to use a combination of Hidden Markov Models and neural nets to perform the gesture recognition. An exemplary application that could be used to implement the resulting models is IBM®'s SPSS (Statistical Package for the Social Sciences). In one exemplary implementation, the performance of a gesture 'x' number of times will generate 'x' sets of data points. The gesture is mapped to a movement of the cursor. The sets of data points can be analyzed to form a statistical model, wherein if a subsequent set of data points relate to each other in a specific way within specific range, it can be determined whether the subsequent set of data points represents the same or statistically similar gesture. "Similar" gestures cause the cursor to move in the manner which was mapped or corresponding to the gesture. A single movement profile may comprise any number of gestures, each corresponding to a different cursor movement. This determination of models/ movement profiles can be thought of as a "training session," and is represented by learn gestures program 112 in FIG. 1.

Different movement profiles may be created for specific injuries, for different body parts, or to change the speed, accuracy, or range of motion required from the gesture to accomplish the same movement of the cursor.

Subsequent to creating the movement profiles, injury prevention and rehabilitation program 110 tracks gestures performed by a user (step 304). As described previously, the gestures are tracked by one or more sensor devices, typically as a plurality of data points relayed to the computer that injury prevention and rehabilitation program 110 operates on. In one embodiment, the sensors transfer the data via a message protocol such as Message Queue Telemetry Transport (MQTT).

Subsequent to any "training" that might occur, i.e., in an operational or usage mode, injury prevention and rehabilitation program 110 moves a cursor on a display device in a manner which corresponds to the gestures (step 306) as determined by a movement profile. In one embodiment, the desired movement profile may be selected by the user. In another embodiment, different movement profiles may be ranked in terms of ease, length of safe use, user preference, etc. For rehabilitation purposes, harder ranked movement profiles may be selected for use more frequently to promote healing. If a user intends to operate the computer for a prolonged period of time, injury prevention and rehabilitation program 110 may select easier ranked movement profiles.

As injury prevention and rehabilitation program 110 tracks gestures and moves the cursor accordingly, the injury prevention and rehabilitation program determines whether there has been any indications that the user is experiencing fatigue or pain (decision 308).

In one embodiment, injury prevention and rehabilitation program 110 can receive a direct notification from the user that the user is experiencing fatigue or pain. For example, the user could select an option displayed on the display device, which when selected would indicate pain. Similarly, a button on a controller attached to the user could be pressed.

In another embodiment, injury prevention and rehabilitation program 110 detects indications of fatigue or pain based on data gathered from the gestures performed. In a first technique, injury prevention and rehabilitation program 110 determines whether the speed of one or more of the performed gestures has fallen below a predetermined speed. The speed of the one or more performed gestures may be derived from a speed of the movement of the cursor, or may be received directly from one or more accelerometers. The predetermined speed may be a predefined value, or may be a value from an average range of speed for the performed gesture, based on a history of the user performing similar gestures.

In a second technique, injury prevention and rehabilitation program 110 determines whether one or more of the performed gestures has fallen below a predefined level of accuracy. In one embodiment, injury prevention and rehabilitation program 110 determines that one or more of the performed gestures have fallen below the predefined level of accuracy when the cursor falls below a level of accuracy in moving to appropriate objects displayed on the display device. In a second embodiment, injury prevention and rehabilitation program 110 determines that one or more of the performed gestures have fallen below the predefined level of accuracy when the injury prevention and rehabilitation program determines that the user is attempting to select, but repeatedly missing, appropriate objects displayed on the display device.

In a third technique, injury prevention and rehabilitation program 110 determines whether the user is experiencing tremors beyond a predefined level when performing the one or more gestures. This may be determined by tracking a gesture performed by the user and determining that data points, within a set of data points representing the gesture, indicate a rate of oscillation in the movement of the gesture beyond a predefined level (even if the set of data points is within the statistical model). In one embodiment, the predefined level may be a value from a range of average oscillation for the user, based on a history of the user performing similar gestures.

Responsive to injury prevention and rehabilitation program 110 receiving an indication that the user is experiencing pain or fatigue (yes branch of decision 308), the injury prevention and rehabilitation program determines a threshold level for potential injury for the gestures performed (the movement profile) (step 310). In one embodiment, the threshold level for potential injury is the maximum continuous period of usage that a user may operate injury prevention and rehabilitation program 110 under the movement profile. The continuous period of usage may be measured by a duration of continuous usage, or alternatively, by a number of performed gestures. If a user subsequently operates the computing device according to the same movement profile, when the user's period of usage nears the threshold level, injury prevention and rehabilitation program 110 can determine that the user is near the point of pain or fatigue. In one embodiment, the threshold level is set at the exact duration of use or number of gestures before the indication of pain or fatigue was indicated. In another embodiment, the threshold level is set lower than the determined period of usage so that a user does not get too close to pain or fatigue.

Alternatively, the threshold level may be one or more of the respective speed, rate of tremors, or level of accuracy at which the user was performing gestures when an indication of pain or fatigue was received.

After determining the threshold level for potential injury for the movement profile, because fatigue or pain was felt, injury prevention and rehabilitation program 110 changes the manner in which the cursor moves in response to gestures performed by the user, i.e., switches to a different movement profile (step 314). For example, where the movement profile is used for rehabilitation purposes, after pain is experienced by the user, injury prevention and rehabilitation program 110 may switch to a movement profile having a difficulty level one below that of the current movement profile. In an alternative embodiment, injury prevention and rehabilitation program 110 may instead request that the user take a break before continuing. The threshold level may be subsequently used to determine if the user, when performing gestures from the selected movement profile, is getting close to pain or fatigue and thus risking injury.

Returning to decision 308, if injury prevention and rehabilitation program 110 determines that no indication of pain or fatigue has been received (no branch of decision 308), the injury prevention and rehabilitation program determines whether subsequent performance of similar gestures (continued gestures from the current movement profile) would be potentially injurious (decision 312). In the preferred embodiment, injury prevention and rehabilitation program 110 uses a threshold level for potential injury, as determined based on previous operation of computing device 102 using gestures under a specific movement profile, to determine if the user is nearing a point of potential injury. As previously discussed, the threshold level may be a period of usage (e.g., duration of use or number of gestures) for the movement profile, a rate of speed, a rate of accuracy, or a rate of tremors.

If injury prevention and rehabilitation program 110 determines that continued performance of similar gestures (operation under the same movement profile) would not be potentially injurious (no branch of decision 312), the injury prevention and rehabilitation program continues to track gestures performed by the user and move the cursor in a corresponding manner. If, on the other hand, injury prevention and rehabilitation program 110 determines that continued performance of similar gestures would be potentially injurious (yes branch of decision 312), the injury prevention and rehabilitation program switches the movement profile (step 314) such that subsequent gestures must differ from the one or more gestures that are potentially injurious to accomplish a similar movement of the cursor. Again, in an alternative embodiment, injury prevention and rehabilitation program 110 may instead recommend to the user to pause or take a break.

In an embodiment designed specifically for rehabilitation, injury prevention and rehabilitation program 110 will increase the threshold level for potential injury for a movement profile after a given number times computing device 102 has been operated under the movement profile without receiving an indication of pain or fatigue from the user. This allows the user to eventually use each movement profile longer, increasing stamina and/or strength over time. Similarly, in other embodiments, if injury prevention and rehabilitation program 110 determines that a user's rate of accuracy or speed is increasing over time, the injury prevention and rehabilitation program can increase the threshold level.

FIG. 4 depicts a block diagram of components of data processing system 100 in accordance with an illustrative embodiment. It should be appreciated that FIG. 4 provides only an illustration of one implementation and does not imply any limitations with regard to the environment in which different embodiments may be implemented. Many modifications to the depicted environment may be made.

Data processing system 100 includes communications fabric 402, which provides communications between processor(s) 404, memory 406, persistent storage 408, communications unit 410, and input/output (I/O) interface(s) 412.

Memory 406 and persistent storage 408 are examples of computer-readable tangible storage devices. A storage device is any piece of hardware that is capable of storing information, such as, data, program code in functional form, and/or other suitable information on a temporary basis and/or permanent basis. Memory 406 may be, for example, one or more random access memories (RAM) 414, cache memory 416, or any other suitable volatile or non-volatile storage device.

Injury prevention and rehabilitation program 110 is stored in persistent storage 408 for execution by one or more of the respective processors 404 via one or more memories of memory 406. In the embodiment illustrated in FIG. 4, persistent storage 408 includes flash memory. Alternatively, or in addition to, persistent storage 408 may include a magnetic disk storage device of an internal hard drive, a solid state drive, a semiconductor storage device, read-only memory (ROM), EPROM, or any other computer-readable tangible storage device that is capable of storing program instructions or digital information.

The media used by persistent storage 408 may also be removable. For example, a removable hard drive may be used for persistent storage 408. Other examples include an optical or magnetic disk that is inserted into a drive for transfer onto another storage device that is also a part of persistent storage 408, or other removable storage devices such as a thumb drive or smart card.

Communications unit 410, in these examples, provides for communications with other computers and devices. In these examples, communications unit 410 includes one or more network interface cards. Communications unit 410 may provide communications through the use of either or both physical and wireless communications links. In another embodiment still, data processing system 100 may be devoid of communications unit 410. Injury prevention and rehabilitation program 110 may be downloaded to persistent storage 408 through communications unit 410.

I/O interface(s) 412 allows for input and output of data with other devices that may be connected to data processing system 100. For example, I/O interface 412 may provide a connection to external devices 418 such as one or more sensors (e.g., sensor(s) 104), a keyboard, keypad, a touch screen, and/or some other suitable input device. I/O interface(s) may also connect to a display device 106. Display device 106 may be, for example, a computer monitor.

The aforementioned programs can be written in various programming languages (such as Java® or C++) including low-level, high-level, object-oriented or non object-oriented languages. Alternatively, the functions of the aforementioned programs can be implemented in whole or in part by computer circuits and other hardware (not shown). In general, the routines executed to implement the embodiments of the present invention, may be part of an operating system or a specific application, component, program, module, object, or sequence of instructions. The programs of the present invention typically are comprised of a multitude of instructions that will be translated by the native computer into a machine-readable format and hence executable instructions. The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Based on the foregoing, a method, computer system, and computer program product have been disclosed for preventing and/or rehabilitating an injury of a user. However, numerous modifications and substitutions can be made without deviating from the scope of the present invention. In this regard, each block in the flowcharts or block diagrams may represent a module, segment, or portion of code, which comprises one or more executable instructions for implementing the specified logical function(s). It should also be noted that, in some alternative implementations, the functions noted in each block may occur out of the order noted in the figures. Therefore, the present invention has been disclosed by way of example and not limitation.

What is claimed is:

1. A method comprising the steps of:
    creating, by a computer, a plurality of movement profiles, each movement profile being in a manner which a cursor moves in response to one or more gestures performed by a user and wherein each movement profile includes one or more different gestures corresponding to a same movement of the cursor, such that a user can perform either at least a first gesture or a second gesture and achieve the same movement of the cursor;
    tracking, via one or more sensor devices connected to the said computer, the one or more gestures performed by a user, wherein a gesture is a detectable movement of a body or a part of the body;
    in response to the tracking of the one or more gestures performed by a user, moving a cursor on a display device of the said computer in a manner which corresponds to both the one or more gestures and at least one movement profile of the plurality of movement profiles indicating a predefined set of one or more gestures that move the cursor;

receiving, based at least on one of data gathered from the gestures performed and a direct notification from the user, an indication that the user is experiencing fatigue or pain;

in response to the received indication that the user is experiencing fatigue or pain, determining, by the said computer, a threshold level for potential injury for the one or more gestures; and using the threshold level to determine if subsequent repeated gestures similar to any of the one or more gestures are nearing a point of potential injury;

in response to receiving no indication that the user is experiencing fatigue or pain, and based at least in part on the at least one movement profile and an analysis of the one or more gestures, determining whether a subsequent performance of one or more of the one or more gestures are potentially injurious;

in response to determining the subsequent gestures would cause the user potential injury, taking, by the said computer, a preventative action, wherein taking the preventative action comprises changing, by the said computer, the at least one movement profile such that subsequent gestures must differ from the one or more potentially injurious gestures to accomplish a similar movement of the cursor.

2. The method of claim 1, wherein the step of taking the preventative action further comprises recommending to the user a pause in making gestures to control the cursor.

3. The method of claim 1, wherein the step of determining whether the subsequent performance of one or more of the one or more gestures are potentially injurious comprises determining, based on a history of the user performing similar gestures to any of the one or more gestures, whether a speed of any of the one or more gestures has reached a threshold level of potential injury.

4. The method of claim 1, wherein the step of determining whether the subsequent performance of one or more of the one or more gestures are potentially injurious comprises determining, based on a history of the user performing similar gestures to any of the one or more gestures, whether an accuracy of any of the one or more gestures has reached a threshold level of potential injury.

5. The method of claim 1, wherein the step of determining whether the subsequent performance of one or more of the one or more gestures are potentially injurious comprises determining, based on a history of the user performing similar gestures to any of the one or more gestures, whether the user is experiencing tremors beyond a predefined level of potential injury.

6. The method of claim 1, wherein the step of determining whether the subsequent performance of one or more of the one or more gestures are potentially injurious comprises determining, based on a history of the user performing similar gestures to any of the one or more gestures, whether a number of the one or more gestures has reached a threshold number of gestures that can be performed before the user experiences pain or fatigue.

7. The method of claim 1, wherein the step of determining whether the subsequent performance of one or more of the one or more gestures are potentially injurious comprises determining, based on a history of the user performing similar gestures to any of the one or more gestures, whether the one or more gestures are performed for a duration of time within a period of usage threshold level that the one or more gestures can be performed before the user experiences pain or fatigue.

8. The method of claim 1, wherein the step of receiving the indication that the user is experiencing fatigue or pain comprises receiving a notification from the user that the user is experiencing fatigue or pain.

9. The method of claim 1, wherein the step of receiving the indication that the user is experiencing fatigue or pain comprises determining one or more of:
   whether any of the one or more gestures is below a predetermined speed;
   whether any of the one or more gestures is below a predefined level of accuracy; and
   whether the tracking of the one or more gestures indicates that the user is experiencing tremors beyond a predefined level.

10. The method of claim 1, wherein the plurality of movement profiles are ranked by a difficulty level.

11. The method of claim 1, wherein the plurality of movement profiles are ranked by one or more of: ease of use, length of safe use, and user preference.

12. The method of claim 1, wherein at least one of at least two different movement profiles enables rehabilitation of an injury to the user.

13. The method of claim 1, wherein the step of changing the at least one movement profile comprises selecting a movement profile that has a lower difficulty level ranking than a current manner movement profile.

14. The method of claim 1, further comprising the step of: determining that a rate of accuracy for the one or more gestures is increased by a predefined level; and in response to the increased rate of accuracy for the one or more gestures, increasing the threshold level for potential injury.

15. The method of claim 1, further comprising the step of: determining that a rate of speed for the one or more gestures is increased by a predefined level; and in response to the increased rate of speed for the one or more gestures, increasing the threshold level for potential injury.

16. The method of claim 1, further comprising the step of: determining that a rate of accuracy or speed for the one or more gestures is increased; and wherein the step of changing the at least one movement profile comprises selecting a movement profile that has a higher difficulty level ranking than a current movement profile.

17. The method of claim 1, further comprising the step of: determining that the one or more gestures are performed for a specified duration without having received an indication of pain or fatigue; and wherein the step of changing the at least one movement profile comprises selecting a movement profile that has a higher difficulty level ranking than a current movement profile.

18. A computer program product comprising:
   one or more non-transitory computer-readable tangible storage devices and program instructions stored on the one or more non-transitory computer-readable tangible storage devices, when executed by one or more computer processors performing the steps of:
   creating a plurality of movement profiles, each movement profile being in a manner which a cursor moves in response to one or more gestures performed by a user and wherein each movement profile includes one or more different gestures corresponding to a same movement of the cursor, such that a user can perform either at least a first gesture or a second gesture and achieve the same movement of the cursor;

tracking, via one or more sensor devices connected to a computer, one or more gestures performed by a user, wherein a gesture is a detectable movement of a body or a part of the body;

in response to the tracking of the one or more gestures performed by a user, moving a cursor on a display device of the said computer in a manner which corresponds to both the one or more gestures and at least one movement profile of the plurality of movement profiles indicating a predefined set of one or more gestures that move the cursor;

receiving, based at least on one of data gathered from the gestures performed and a direct notification from the user, an indication that the user is experiencing fatigue or pain;

in response to the received indication that the user is experiencing fatigue or pain, determining, by the said computer, a threshold level for potential injury for the one or more gestures; and using the threshold level to determine if subsequent repeated gestures, similar to any of the one or more gestures, are nearing a point of potential injury;

in response to receiving no indication that the user is experiencing fatigue or pain, and based, at least in part on the at least one movement profile and an analysis of the one or more gestures, determining whether a subsequent performance of one or more of the one or more gestures are potentially injurious;

in response to determining the subsequent gestures would cause the user potential injury, taking, by the said computer, a preventative action, wherein taking the preventative action comprises changing, by the said computer, the at least one movement profile such that subsequent gestures must differ from the one or more potentially injurious gestures to accomplish a similar movement of the cursor.

19. A computer system comprising:

one or more computer processors;

one or more non-transitory computer-readable tangible storage devices;

program instructions stored on the one or more non-transitory computer-readable tangible storage devices for execution by at least one of the one or more computer processors, the stored program instructions comprising:

program instructions to create a plurality of movement profiles, each movement profile being in a manner in which a cursor moves in response to one or more gestures performed by a user and wherein each movement profile includes one or more different gestures corresponding to a same movement of the cursor, such that a user can perform either at least a first gesture or a second gesture and achieve the same movement of the cursor;

program instructions to track, via one or more sensor devices connected to a computer, one or more gestures performed by a user, wherein a gesture is a detectable movement of a body or a part of the body;

program instructions to move, in response to the tracked of the one or more gestures performed by a user, a cursor on a display device of the said computer in a manner which corresponds to both the one or more gestures and at least one movement profile of the plurality of movement profiles indicating a predefined set of one or more gestures that move the cursor;

program instructions to receive, based at least on one of data gathered from the gestures performed and a direct notification from the user, an indication that the user is experiencing fatigue or pain;

program instructions to determine, in response to the received indication that the user is experiencing fatigue or pain, a threshold level for potential injury for the one or more gestures; and program instructions to use the threshold level to determine if subsequent repeated gestures, similar to any of the one or more gestures, are nearing a point of potential injury;

program instructions to determine, in response to no received indication that the user is experiencing fatigue or pain, and based, at least in part on the at least one movement profile and an analysis of the one or more gestures, whether a subsequent performance of one or more of the one or more gestures are potentially injurious;

program instructions to in response to the determination of the subsequent gestures would cause the user potential injury, take, by the said computer, a preventative action, wherein take the preventative action comprises program instructions to change, by the said computer, the at least one movement profile such that subsequent gestures must differ from the one or more potentially injurious gestures to accomplish a similar movement of the cursor.

20. The method of claim 1, wherein moving the cursor on a said display device of the said computer in a manner which corresponds to both the one or more gestures and at least one movement profile of the plurality of movement profiles includes a ratio of gesture movement to cursor movement greater than one-to-one or less than one-to-one.

* * * * *